(12) United States Patent
Tohyama et al.

(10) Patent No.: US 7,223,862 B2
(45) Date of Patent: *May 29, 2007

(54) PYRIDONE COMPOUNDS USEFUL FOR PRODUCING PYRIDINE COMPOUNDS

(75) Inventors: Yoshitomo Tohyama, Ashiya (JP); Takashi Komori, Osaka (JP); Yuzuru Sanemitsu, Hyogo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/382,354

(22) Filed: May 9, 2006

(65) Prior Publication Data

US 2006/0189484 A1 Aug. 24, 2006

Related U.S. Application Data

(63) Continuation of application No. 10/486,037, filed as application No. PCT/JP02/07793 on Jul. 31, 2002.

(30) Foreign Application Priority Data

Aug. 2, 2001 (JP) ............................. 2001-234650
Mar. 27, 2002 (JP) ............................. 2002-088577

(51) Int. Cl.
    C07D 401/12 (2006.01)
(52) U.S. Cl. ..................................... 544/310
(58) Field of Classification Search ................. 544/310
    See application file for complete search history.

(56) References Cited

U.S. PATENT DOCUMENTS

| 4,859,229 | A | 8/1989 | Wenger |
| 5,008,267 | A | 4/1991 | Katakami |
| 6,537,948 | B1 * | 3/2003 | Tohyama et al. ........... 504/243 |

FOREIGN PATENT DOCUMENTS

| EP | 255047 A1 | 2/1998 |
| EP | 1122244 A1 * | 8/2001 |
| WO | 98/41093 A1 | 9/1998 |
| WO | 01/77084 A1 | 10/2001 |

OTHER PUBLICATIONS

M.P. Cava, "Pyridine Derivatives, II", Journal of Organic Chemistry, vol. 23, No. 11, (1958).
Nishiyama, H., et al., "Reaction of Some Amides and Thioamides with Diazomethane Catalyzed by Silica Gel", Tetrahedron Letters, No. 48, pp. 4671-4674 (1979).
Busch-Petersen, J., et al., "A Rhodium (II) Catalytic Approach to the Synthesis of Ethers of a Minor Component in a Tautomeric Set", Organic Letters, vol. 2, No. 11, pp. 1641-1643 (2000).

* cited by examiner

Primary Examiner—Deepak Rao
(74) Attorney, Agent, or Firm—Akin Gump Strauss Hauer & Feld LLP

(57) ABSTRACT

The present invention provides a process for producing the pyridine compound [d]:

[d]

[wherein $R^3$ and $R^4$ are as defined below], which has an excellent herbicidal activity, by making a pyridine compound [a]:

[a]

[wherein $R^1$ represents a C1–C6 alkoxy group, $R^3$ represents a halogen atom, cyano group or nitro group, and $R^4$ ρεπρεσεντσ α ηψδρογεν ατομ ορ ηαλογεν ατομ] ρεαχτ ωιτη αν α-diazoester compound [f]:

$N_2CHCOR^1$ [f]

[wherein $R^1$ is defined above]
in the presence of an acid.

3 Claims, No Drawings

PYRIDONE COMPOUNDS USEFUL FOR PRODUCING PYRIDINE COMPOUNDS

CROSS-REFERENCE TO RELATED APPLICATIONS

This application is a continuation of U.S. patent application Ser. No. 10/486,037, filed Feb. 6, 2004, which is a Section 371 of International Application No. PCT/JP02/07793, filed Jul. 31, 2002, the entire contents of each of which are herein incorporated by reference.

BACKGROUND OF THE INVENTION

The present invention relates to a novel process for producing pyridine compounds having excellent herbicidal activity and starting compounds for the process.

The pyridine compounds [d]:

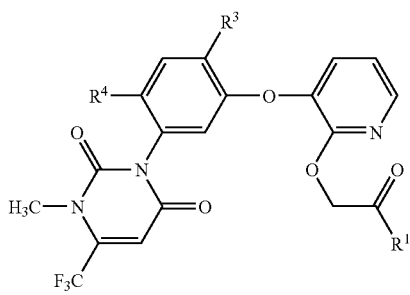

[d]

wherein $R^1$ represents a C1–C6 alkoxy group, $R^3$ represents a halogen atom, cyano group or nitro group, and $R^4$ represents a hydrogen atom or halogen atom have excellent herbicidal activity. The pyridine compounds [d] contain two heterocyclic rings which are uracil ring and pyridine ring, and a beneficial process to produce them is desired. The object of the present invention is to provide a beneficial process for producing the pyridine compounds [d] having a specific pattern of substituents and starting compounds for the process.

DISCLOSURE OF THE INVENTION

The present inventors earnestly studied to find a beneficial process for producing the pyridine compounds [d]. As a result, they have found that the pyridine compound [d] can be produced by making a pyridone compound [a]:

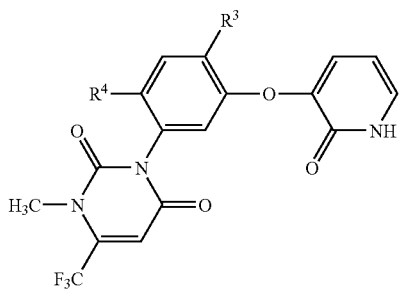

[a]

wherein $R^3$ and $R^4$ represent the same meanings as defined above react with an α-diazoester compound [f]:

$N_2CHCOR^1$     [f]

wherein $R^1$ represents the same meaning as defined above in the presence of an acid to proceed regioselective O-alkylation, and completed the present invention. By adopting the present process, the pyridine compound [d] having the specific pattern of the substituents can be produced beneficially.

Namely, the present invention provides a process for producing the pyridine compound [d] by making the pyridone compound [a] react with the α-diazoester compound [f] in the presence of an acid (hereinafter, referred to as the process of the present invention) and the pyridone compound [a] that is an important starting compound for the process.

In the present invention, examples of the C1–C6 alkoxy group given for $R^1$ include methoxy group, ethoxy group, propoxy group and so on, and examples of the halogen atom given for $R^3$ and $R^4$ include fluorine atom, chlorine atom and bromine atom.

The process of the present invention is carried out by making the pyridone compound [a] react with the α-diazoester compound [f] in the presence of an acid, and the reaction is usually performed in a solvent. Examples of the solvent include aromatic hydrocarbons such as benzene, toluene, xylene and so on; halogenated hydrocarbons such as 1,2-dichloroethane, chlorobenzene, dichlorobenzene and so on; and mixtures thereof.

In the present method, the acid means an acid defined by G. N. Lewis, namely a substance that can accept electron, and includes aprotic acid and protic acid (Brønsted acid). Examples of the aprotic acid include rhodium (II) salts, boron trifluoride and tin tetrachloride, and examples of protic acid include sulfonic acids such as trifluoromethanesulfonic acid, p-toluenesulfonic acid, and so on; trifluoroacetic acid; and sulfuric acid. The rhodium (II) salts means a metal salt of divalent rhodium cation and an appropriate anion, optionally further an appropriate ligand, and typical examples are rhodium (II) trifluoroacetate dimmer ($[(CF_3CO_2)_2Rh]_2$), rhodium (II) acetate dimmer ($[(CH_3CO_2)_2Rh]_2$) and so on. As the boron trifluoride, $BF_3$ itself or its complex can be utilized, and examples of the complex include diethyl ether complex, dimethyl sulfide complex, tetrahydrofuran complex and so on. In the view of reaction rate, it is preferable to use rhodium (II) trifluoroacetate dimmer, boron trifluoride/diethyl ether complex, tin tetrachloride or trifluoromethanesulfonic acid as an acid.

In the present reaction, one mole of the α-diazoester compound [f] is theoretically needed based on one mole of the pyridone compound [a], and practically 1 to 2 moles of the α-diazoester compound [f] are used. In the present reaction, the acid has a catalytic activity and the amount in the range of 0.001 to 5 moles, preferably 0.01 mole or more in the view of the reaction rate, is used based on one mole of the pyridone compound [a]. The reaction temperature of the present reaction is usually −50 to 120° C., preferably −20° C. or more in the view of the reaction rate. The reaction time is usually in the range of momentarily to 72 hours.

The reagents utilized for the present reaction are added into a reaction vessel, for example, in the following order.
1) A method of mixing the pyridone compound [a], an acid and a solvent in advance, and adding the α-diazoester compound [f] dropwise therein.
2) A method of mixing the pyridone compound [a], the α-diazoester compound [f] and a solvent in advance, and adding an acid dropwise therein.
3) A method of mixing the pyridone compound [a] and a solvent in advance, and adding an acid and the α-diazoester compound [f] dropwise therein respectively.

The end point of the present reaction can be detected by sampling a part of the reaction mixture, analyzing the sample by liquid chromatography, thin-layer chromatography and so on, and measuring the remained amount of the pyridone compound [a] or the α-diazoester compound [f].

After the reaction, the pyridine compound [d] can be obtained, for example, by subjecting the reaction mixture to the following work-up procedures:
1) filtering the reaction mixture and concentrating the filtrate.
2) subjecting the reaction mixture to silica gel chromatography, and then concentration.
3) pouring the reaction mixture to aqueous sodium bicarbonate solution, extracting with an organic solvent, and drying and concentrating the organic layer.

The obtained pyridine compound [d] can be purified by a procedure such as chromatography, recrystallization and so on.

In case making the pyridone compound [a] react with an ester compound [x]:

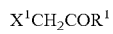  [x]

[wherein $R^1$ represents the same meaning as defined above and $X^1$ represents a chlorine atom, bromine atom, methanesulfonyloxy group or p-toluenesulfonyloxy group]

in the presence of a base, a pyridone compound [y]:

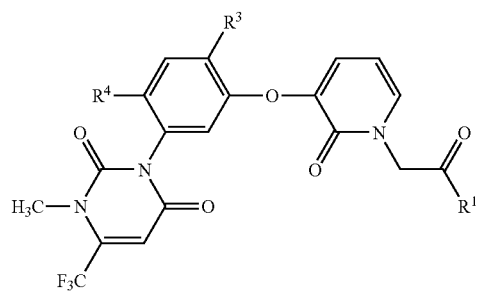

[wherein $R^3$, $R^4$ and $R^1$ represent the same meanings as defined above] was a main product.

The α-diazoester compound [f] utilized for the present invention is on sale itself, or can be prepared by a known method of making a compound [h]:

  [h]

[wherein $R^1$ represents the same meaning as defined above]

or its mineral acid salt (i.e. hydrochloride salt) react with sodium nitrite under an acidic condition. (See Organic Syntheses Collective Volume IV p. 424–426.)

The α-diazoester compound [f] obtained by making the compound [h] or its mineral acid salt react with sodium nitrite under an acidic condition can be used as a starting material for the process of the present invention without isolation. Namely, a solution of the α-diazoester compound [f], which is obtained by making the α-diazoester compound [h] react with sodium nitrite under an acidic condition, extracting with an organic solvent, can be provided to the process of the present invention after an appropriate treatment such as drying with anhydrous magnesium sulfate. Example of the organic solvent used above include aromatic hydrocarbons such as benzene, toluene, xylene and so on; and halogenated hydrocarbons such as dichloromethane, 1,2-dichloroethane, chlorobenzene, dichlorobenzene, benzotrifluoride and so on.

The pyridone compound [a] used for the process of the present invention can be prepared from a known compound by the following methods.

Preparation Method 1

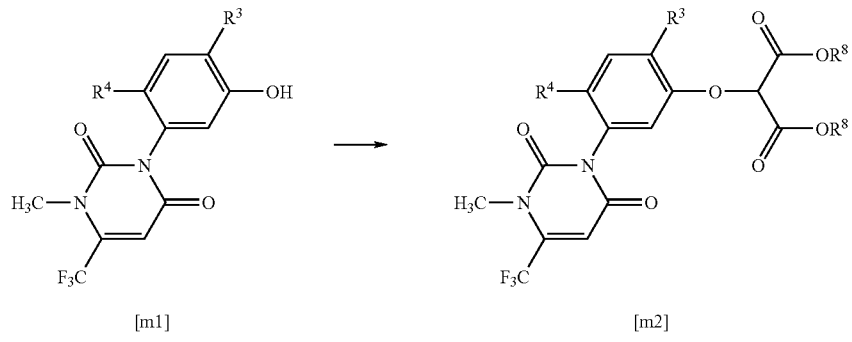

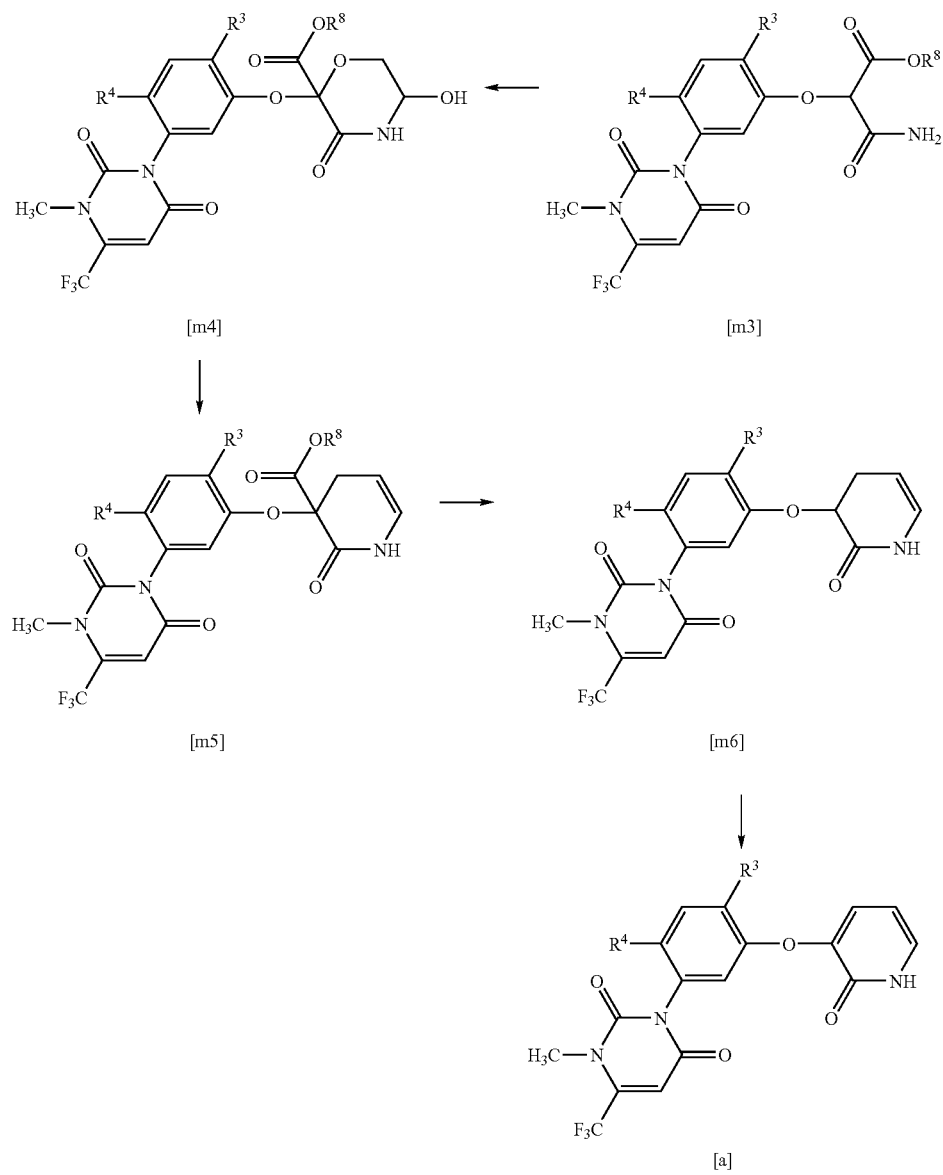

[wherein $R^3$ and $R^4$ represent the same meanings as defined above and $R^8$ represents a lower alkyl group such as methyl group, ethyl group and so on]

Compound [m1]→Compound [m2]

Compound [m2] is prepared by making Compound [m1] react with Compound [m7]:

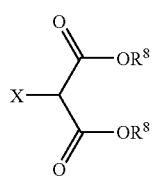

[wherein $R^8$ represents the same meaning as defined above and X represents a leaving group such as chlorine atom, bromine atom and so on] in the presence of a base.

The reaction is usually carried out in a solvent. The reaction temperature is usually in the range of room temperature to 80° C. and the reaction time is usually in the range of momentarily to 12 hours.

In the reaction, one mole of Compound [m7] and one mole of the base are theoretically needed based on one mole of Compound [m1], but the amounts may be freely varied according to the condition.

Examples of the base used for the reaction include potassium carbonate and examples of the solvent include nitrites such as acetonitrile and so on; and acid amides such as N,N-dimethylformamide, N-methyl-2-pyrrolidone and so on.

After the reaction, the reaction mixture is filtered if necessary, and the filtrate is concentrated; the reaction mixture is poured into water or acidic water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [m2]→Compound [m3]

Compound [m3] is prepared by making Compound [m2] react with ammonia.

The reaction is usually carried out in a solvent. The reaction temperature is usually in the range of −20 to 50° C. and the reaction time is usually in the range of momentarily to 12 hours.

In the reaction, one mole of ammonia is theoretically needed based on one mole of Compound [m2], but the amount may be freely varied according to the condition.

Examples of the solvent used for the reaction include alcohols such as methanol, ethanol and so on.

After the reaction, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [m1]→Compound [m3]

Compound [m3] is prepared by making Compound [m1] react with Compound [m8]:

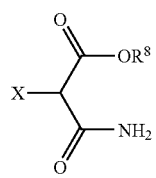

[m8]

[wherein $R^8$ and X represent the same meanings as defined above] in the presence of a base.

The reaction is usually carried out in a solvent. The reaction temperature is usually in the range of room temperature to 80° C. and the reaction time is usually in the range of momentarily to 12 hours.

In the reaction, one mole of Compound [m8] and one mole of the base are theoretically needed based on one mole of Compound [m1], but the amounts may be freely varied according to the condition.

Examples of the base used for the reaction include potassium carbonate and examples of the solvent include nitrites such as acetonitrile and so on; and acid amides such as N,N-dimethylformamide, N-methyl-2-pyrrolidone and so on.

After the reaction, the reaction mixture is filtered if necessary, and the filtrate is concentrated; the reaction mixture is poured into water or acidic water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [m3]→Compound [m4]

Compound [m4] is prepared by making Compound [m3] react with acrolein in the presence of a base.

The reaction is usually carried out in a solvent. The reaction temperature is usually in the range of −30 to 50° C., preferably −10 to 20° C. The reaction time is usually in the range of momentarily to 12 hours.

In the reaction, one mole of acrolein and 0.01 to 2 moles of the base are theoretically needed based on one mole of Compound [m3], but the amounts may be freely varied according to the condition.

Examples of the base used for the reaction include metal alkoxides such as potassium t-butoxide and so on; and inorganic bases such as potassium carbonate and so on.

Examples of the solvent used for the reaction include ethers such as tetrahydrofuran and so on; and esters such as ethyl acetate and so on.

After the reaction, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [m4]→Compound [m5]

Compound [m5] is prepared by making Compound [m4] react in the presence of an acid.

The reaction is usually carried out in a solvent. The reaction temperature is usually in the range of room temperature to 150° C. and the reaction time is usually in the range of momentarily to 24 hours.

In the reaction, 0.001 to 0.2 mole of the acid is utilized based on one mole of Compound [m4], but the amount may be freely varied according to the condition.

Examples of the acid used for the reaction include organic acids such as acetic acid, p-toluenesulfonic acid and so on; and inorganic acids such as hydrochloric acid and so on. Examples of the solvent include ethers such as tetrahydrofuran and so on; and esters such as ethyl acetate and so on.

After the reaction, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [m5]→Compound [m6]

Compound [m6] is prepared by making Compound [m5] react in the presence of water and alkali metal halide, usually in a solvent.

The reaction temperature is usually in the range of 80 to 140° C. and the reaction time is usually in the range of momentarily to 48 hours.

In the reaction, 0.5 to 2 moles of water and 1 to 5 moles of the alkali metal halide is utilized based on one mole of Compound [m5], but the amounts may be freely varied according to the condition.

Examples of the alkali metal halide used for the reaction include lithium chloride, sodium chloride, lithium iodide and sodium iodide and examples of the solvent include dimethyl sulfoxide and pyridine.

After the reaction, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [m6]→the pyridone compound [a]

The pyridone compound [a] is prepared by making Compound [m6] react with a dehydrogenation agent.

The reaction is usually carried out in a solvent. The reaction temperature is usually in the range of 60 to 190° C. and the reaction time is usually in the range of momentarily to 48 hours.

The dehydrogenation agent used for the present reaction means quinine oxidizing agents such as chloranile and so on; and heterogeneous metal catalyst such as palladium/carbon and so on.

In the reaction, 1 to 3 moles of the quinine oxidizing agent or 10 to 30% by weight of the heterogeneous metal catalyst is utilized based on one mole of Compound [m6], but the amount may be freely varied according to the condition.

Examples of the solvent include aromatic hydrocarbons such as toluene, xylene and so on; halogenated aromatic hydrocarbons such as chlorobenzene, dichlorobenzene, benzotrifluoride and so on; ethers such as dioxane, tetrahydrofuran, diglyme, diphenyl ether and so on; and mixtures thereof.

After the reaction, the reaction mixture is filtered if necessary, and the filtrate is concentrated; the reaction mixture is diluted with an organic solvent, then poured into aqueous sodium bicarbonate solution, extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [m1] is known in U.S. Pat. No. 4,859,229, and it can be prepared by the known method or the like.

Compound [m7] is on sale itself or it can be prepared by the known method.

Compound [m8] can be prepared by making Compound [m7] react with ammonia under the above "Compound [m2]→Compound [m3]" reaction condition.

Preparation Method 2

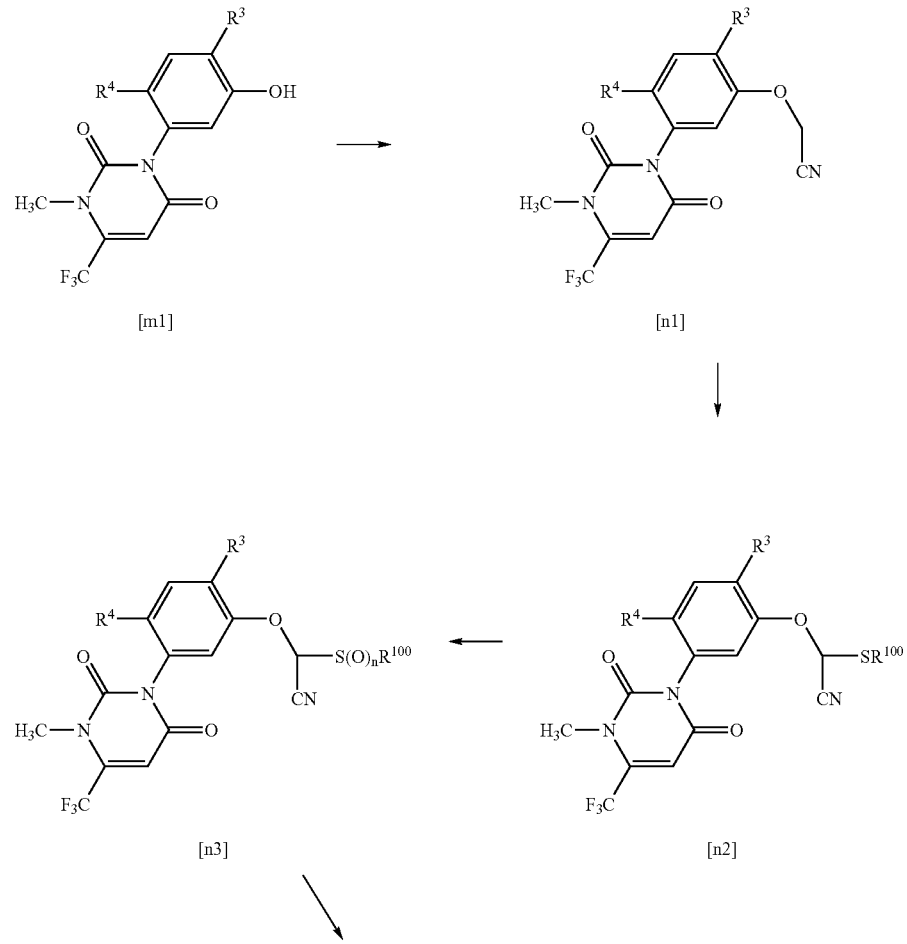

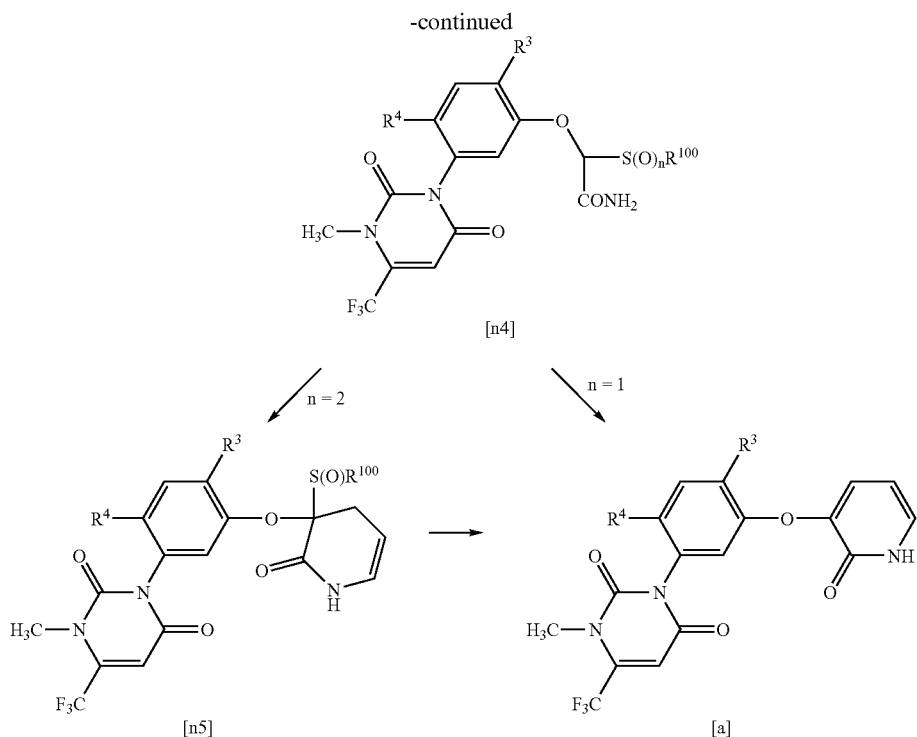

[wherein $R^3$ and $R^4$ represent the same meanings as defined above; $R^{100}$ represents a lower alkyl group such as methyl group, ethyl group and so on, or phenyl group; and n represents 1 or 2]

Compound [m1]→Compound [n1]

Compound [n1] can be prepared by making Compound [m] react with chloroacetonitrile or bromoacetonitrile in the presence of a base.

The reaction is carried out in a solvent. The reaction temperature is usually in the range of −20 to 80° C. and the reaction time is usually in the range of momentarily to 24 hours.

In the reaction, one mole of chloroacetonitrile or bromoacetonitrile and one mole of the base are theoretically needed based on one mole of Compound [m1], but the amounts may be freely varied according to the condition.

Examples of the base used for the reaction include sodium hydride, potassium carbonate, sodium bicarbonate, sodium hydride and potassium hydroxide, and examples of the solvent include nitrites such as acetonitrile and so on; acid amides such as N,N-dimethylformamide, N-methyl-2-pyrrolidone and so on; ethers such as tetrahydrofuran, 1,4-dioxane, ethylene glycol dimethyl ether, 2-methoxyethyl ether and so on; hydrocarbons such as toluene and so on; and esters such as methyl acetate, ethyl acetate and so on.

After the reaction, the reaction mixture is filtered if necessary, and the filtrate is concentrated; the reaction mixture is poured into water or acidic water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [n1]→Compound [n2]

Compound [n2] can be prepared by making Compound [n1] react with a disulfide compound [n6]:

$$(R^{100}S)_2 \qquad [n6]$$

[wherein $R^{100}$ represents the same meaning as defined above] in the presence of a base.

The reaction is usually carried out in a solvent. The reaction temperature is usually in the range of −50 to 10° C. and the reaction time is usually in the range of momentarily to 12 hours.

In the reaction, one mole of the disulfide compound [n6] is theoretically needed based on one mole of Compound [n1], but the amount may be freely varied according to the condition.

Examples of the solvent include acid amides such as DMF, N-methylpyrrolidin-2-one and so on.

After the reaction, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [n2]→Compound [n3]

Compound [n3] can be prepared by making Compound [n2] react with an oxidizing agent.

The reaction is usually carried out in a solvent. The reaction temperature is usually in the range of −20 to 50° C. and the reaction time is usually in the range of momentarily to 24 hours.

The oxidizing agent is peracids such as m-chloroperbenzoic acid and so on; and hydrogen peroxide. Examples of the solvent used for the reaction include halogenated compounds such as chloroform, dichloromethane and so on.

In the reaction, one and two moles of the oxidizing agent are theoretically needed based on one mole of Compound [n2] when n=1 and n=2 respectively, but the amount may be freely varied according to the condition.

After the reaction, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [n3]→Compound [n4]

Compound [n4] can be prepared by making Compound [n3] react in the presence of water and manganese dioxide.

The reaction is usually carried out in a solvent. The reaction temperature is usually in the range of 50 to 120° C. and the reaction time is usually in the range of momentarily to 24 hours.

In the reaction, the manganese dioxide is used in the amount of a catalytic amount to excess.

Examples of the solvent used for the reaction include water and mixtures of water with organic solvent (alcohols such as methanol, ethanol, isopropanol and so on; ketones such as acetone, methyl ethyl ketone, methyl isobutyl ketone and so on; and ethers such as tetrahydrofuran, 1,4-dioxane and so on).

After the reaction, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Furthermore, Compound [n4] is also prepared by making Compound [n3] react in the presence of water and sodium tetraborate.

Compound [n4]→the pyridone compound [a]

The pyridone compound [a] can be prepared by making Compound [n4], wherein n is 1, react with acrolein in the presence of a base and then react in the presence of an acid.

The reaction is usually carried out in a solvent. The reaction temperature of the first step is in the range of −20 to 50° C. and the reaction temperature of the second step is in the range of room temperature to 80° C. The reaction time is usually in the range of momentarily to 48 hours.

Examples of the base used for the reaction include sodium hydride, potassium t-butoxide, sodium hydroxide, potassium carbonate, potassium fluoride and so on, and examples of the acid include acetic acid, trifluoroacetic acid, methanesulfonic acid, p-toluenesulfonic acid, boron trifluoride and complex thereof (e.g. boron trifluoride-methanol complex). Examples of the solvent include ethers such as diethyl ether, methyl t-butyl ether, dimethoxyethane, tetrahydrofuran, 1,4-dioxane and so on; halogenated compounds such as chloroform, dichloromethane and so on; and hydrocarbons such as toluene and so on.

In the reaction, the amounts of the base and acid are a catalytic amount to one equivalent and a catalytic amount to excess, respectively, and one mole of the acrolein is theoretically needed based on one mole of Compound [n4], but the amounts may be freely varied according to the condition.

After the reaction, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [n4]→Compound [n5]

Compound [n5] can be prepared by making Compound [n4], wherein n is 2, react with acrolein in the presence of a base and then react in the presence of an acid.

The reaction is usually carried out in a solvent. The reaction temperature of the first step is in the range of −20 to 50° C. and the reaction temperature of the second step is in the range of room temperature to 50° C. The reaction time is usually in the range of momentarily to 48 hours.

Examples of the base used for the reaction include sodium hydride, potassium t-butoxide, sodium hydroxide, potassium carbonate, potassium fluoride and so on, and examples of the acid include acetic acid, trifluoroacetic acid, methanesulfonic acid, p-toluenesulfonic acid, boron trifluoride and complex thereof (e.g. boron trifluoride-methanol complex). Examples of the solvent include ethers such as diethyl ether, methyl t-butyl ether, dimethoxyethane, tetrahydrofuran, 1,4-dioxane and so on; halogenated compounds such as chloroform, dichloromethane and so on; and hydrocarbons such as toluene and so on.

In the reaction, the amounts of the base and acid are a catalytic amount to one equivalent and a catalytic amount to excess, respectively, and one mole of the acrolein is theoretically needed based on one mole of Compound [n4], but the amounts may be freely varied according to the condition.

Compound [n5]→the pyridone compound [a]

The pyridone compound [a] can be prepared by making Compound [n5] react in the presence an acid.

The reaction is usually carried out in a solvent. The reaction temperature is in the range of 50 to 130° C. and the reaction time is usually in the range of momentarily to 48 hours.

Examples of the acid include acetic acid, trifluoroacetic acid, methanesulfonic acid, p-toluenesulfonic acid, boron trifluoride and complex thereof (e.g. boron trifluoride-methanol complex). Examples of the solvent include sulfur compounds such as dimethyl sulfoxide and so on; ether compounds such as dimethoxyethane, tetrahydrofuran, 1,4-dioxane and so on; and hydrocarbons such as toluene and so on.

In the reaction, the acid is used at an amount of a catalytic amount to excess.

After the reaction, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Further, Compound [n4] is also prepared by the following method:

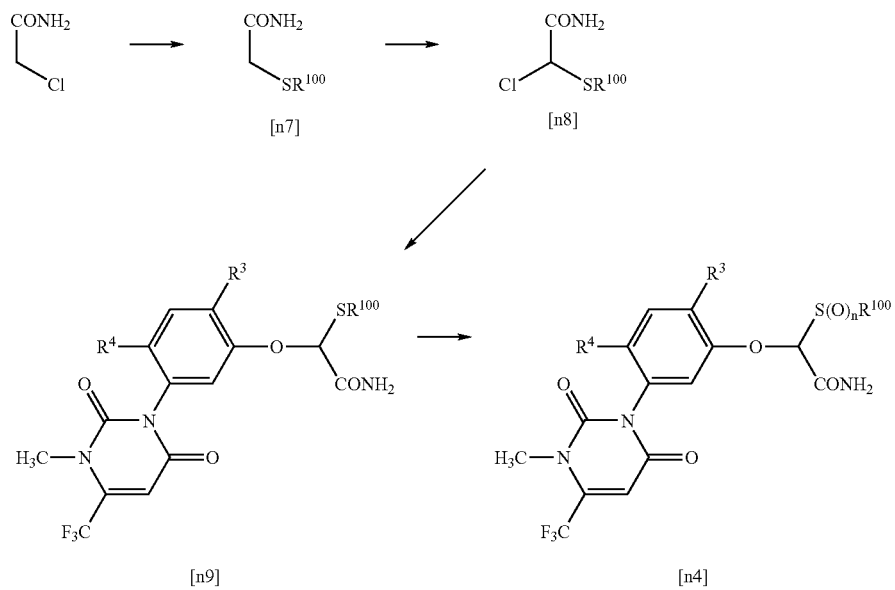

[wherein $R^3$, $R^4$ and $R^{100}$ represent the same meanings as defined above]

2-chloroacetamide→Compound [n7]

Compound [n7] can be prepared by making Compound [n10]:

NaSR$^{100}$      [n10]

[wherein $R^{100}$ represents the same meaning as defined above] react with 2-chloroacetamide.

The reaction is usually carried out in a solvent. The reaction temperature is in the range of room temperature to 50° C. and the reaction time is usually in the range of momentarily to 48 hours.

Examples of the solvent include alcohols such as methanol, ethanol, isopropanol and so on; water; and mixtures thereof.

In the reaction, one mole of Compound [n10] is theoretically needed based on one mole of 2-chloroacetamide, but the amount may be freely varied according to the condition.

After the reaction, the reaction mixture is concentrated as it is; or after the one mole reaction of the 2-chloroacetamide, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [n7]→Compound [n8]

Compound [n8] can be prepared by making Compound [n7] react with a chlorinating agent.

The reaction is usually carried out in a solvent. The reaction temperature is in the range of −10 to 30° C. and the reaction time is usually in the range of momentarily to 48 hours.

Examples of the solvent include halogen compounds such as chloroform, dichloromethane, and examples of the chlorinating agent include sulfuryl chloride.

In the reaction, one mole of the chlorinating agent is theoretically needed based on one mole of Compound [n7], but the amount may be freely varied according to the condition.

After the reaction, the reaction mixture is concentrated as it is; or after the one mole reaction of the chlorinating agent, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [n8]→Compound [n9]

Compound [n9] can be prepared by making Compound [n8] react with Compound [m1] in the presence of a base and optionally further iodide salt.

The reaction is usually carried out in a solvent. The reaction temperature is in the range of −10 to 80° C. and the reaction time is usually in the range of momentarily to 48 hours.

Examples of the solvent include ketones such as acetone, methyl ethyl ketone, methyl isobutyl ketone and so on; sulfur compounds such as dimethyl sulfoxide and so on; ethers such as diethyl ether, methyl t-butyl ether, dimethoxyethane, tetrahydrofuran, 1,4-dioxane and so on; and hydrocarbons such as toluene. Examples of the base include sodium hydride, potassium carbonate, sodium bicarbonate, sodium hydroxide and potassium t-butoxide, and examples of the iodide salt include sodium iodide and potassium iodide.

In the reaction, one mole of Compound [m1] is theoretically needed based on one mole of Compound [n8] and one mole of the base is theoretically needed based on one mole of Compound [m1], but the amounts may be freely varied according to the condition.

After the reaction, the reaction mixture is concentrated as it is; or after the one mole reaction of Compound [n8], the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

Compound [n9]→Compound [n4]

Compound [n4] can be prepared by making Compound [n9] react with an oxidizing agent.

The reaction is usually carried out in a solvent. The reaction temperature is in the range of −30 to 50° C. and the reaction time is usually in the range of momentarily to 24 hours.

The oxidizing agent is peracids such as m-chloroperbenzoic acid and so on; and hydrogen peroxide. Examples of the solvent used for the reaction include halogenated compounds such as chloroform, dichloromethane and so on.

In the reaction, one and two moles of the oxidizing agent are theoretically needed based on one mole of Compound [n9] when n=1 and n=2 respectively, but the amount may be freely varied according to the condition.

After the reaction, the reaction mixture is filtered if necessary, and the filtrate is concentrated; the reaction mixture is poured into water and the precipitated crystals are collected by filtration; or the reaction mixture is extracted with an organic solvent, the organic layer is dried and subjected to usual work-up procedures such as concentration and so on to give an objective compound. Further, it is possible to purify the obtained compound by the procedures such as chromatography, recrystallization and so on.

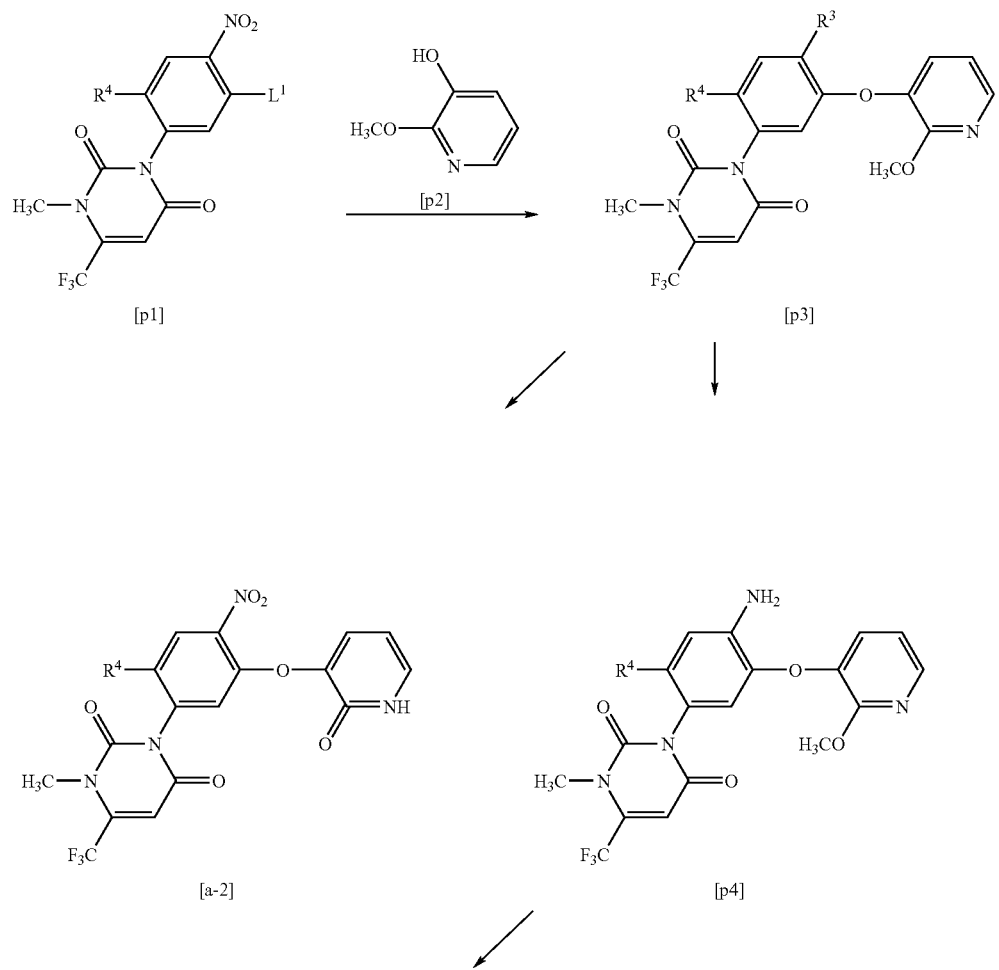

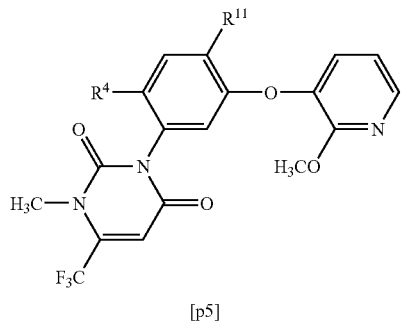

[p5]

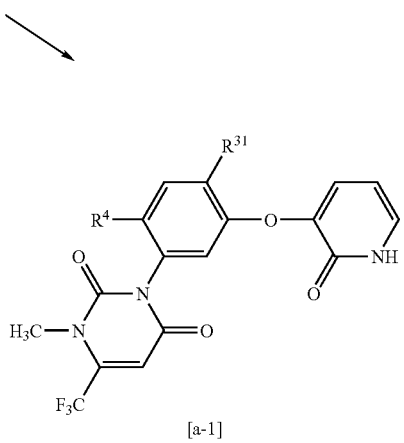

[a-1]

[wherein $R^4$ represents the same meaning as defined above, $R^{31}$ represents a halogen atom or cyano group and $L^1$ represents a fluorine atom or chlorine atom]

Compound [p1]→Compound [p3]

Compound [p3] can be prepared by making Compound [p1] and Compound [p2] react with a base such as potassium carbonate usually in a solvent.

Compound [p3]→Compound [p4]

Compound [p4] can be prepared by making Compound [p3] react under hydrogen atmosphere in the presence of a catalyst such as palladium/carbon and so on usually in a solvent, or react with iron powder in a mixed solvent of acetic acid with water.

Compound [p4]→Compound [p5]

Compound [p5] can be prepared by making Compound [p4] react with a diazotizing agent such as sodium nitrate and so on, and then react with copper chloride, copper bromide or copper cyanide in a solvent.

Compound [p5]→Compound [a-1]

The pyridone compound [a] wherein $R^3$ represents a halogen atom or cyano group, namely the pyridone compound [a-1], can be prepared by making Compound [p5] react with boron tribromide usually in a solvent.

Compound [p3]→Compound [a-2]

The pyridone compound [a] wherein $R^3$ represents a nitro group, namely the pyridone compound [a-2], can be prepared by making Compound [p3] react with boron tribromide usually in a solvent.

Compound [p2] can be prepared by the following method:

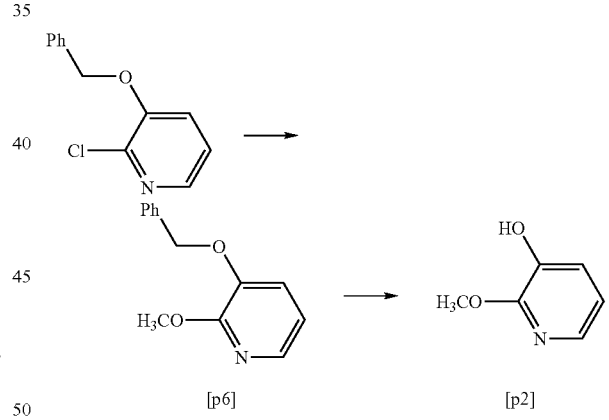

[p6]     [p2]

2-chloro-3-benzyloxypyridine→Compound [p6]

Compound [p6] can be prepared by making 2-chloro-3-benzyloxypyridine react with methanol in the presence of a base usually in a solvent.

Compound [p2]→Compound [p6]

Compound [p6] can be prepared by making Compound [p2] react under hydrogen atmosphere in the presence of a catalyst such as palladium/carbon and so on usually in a solvent.

Further, Compound [p2] can be also prepared by the method described in U.S. Pat. No. 3,701,779 or its modification.

2-Chloro-3-benzyloxypyridine can be prepared by the method described in Heterocycles 1994, 38(6), 1355–1360.

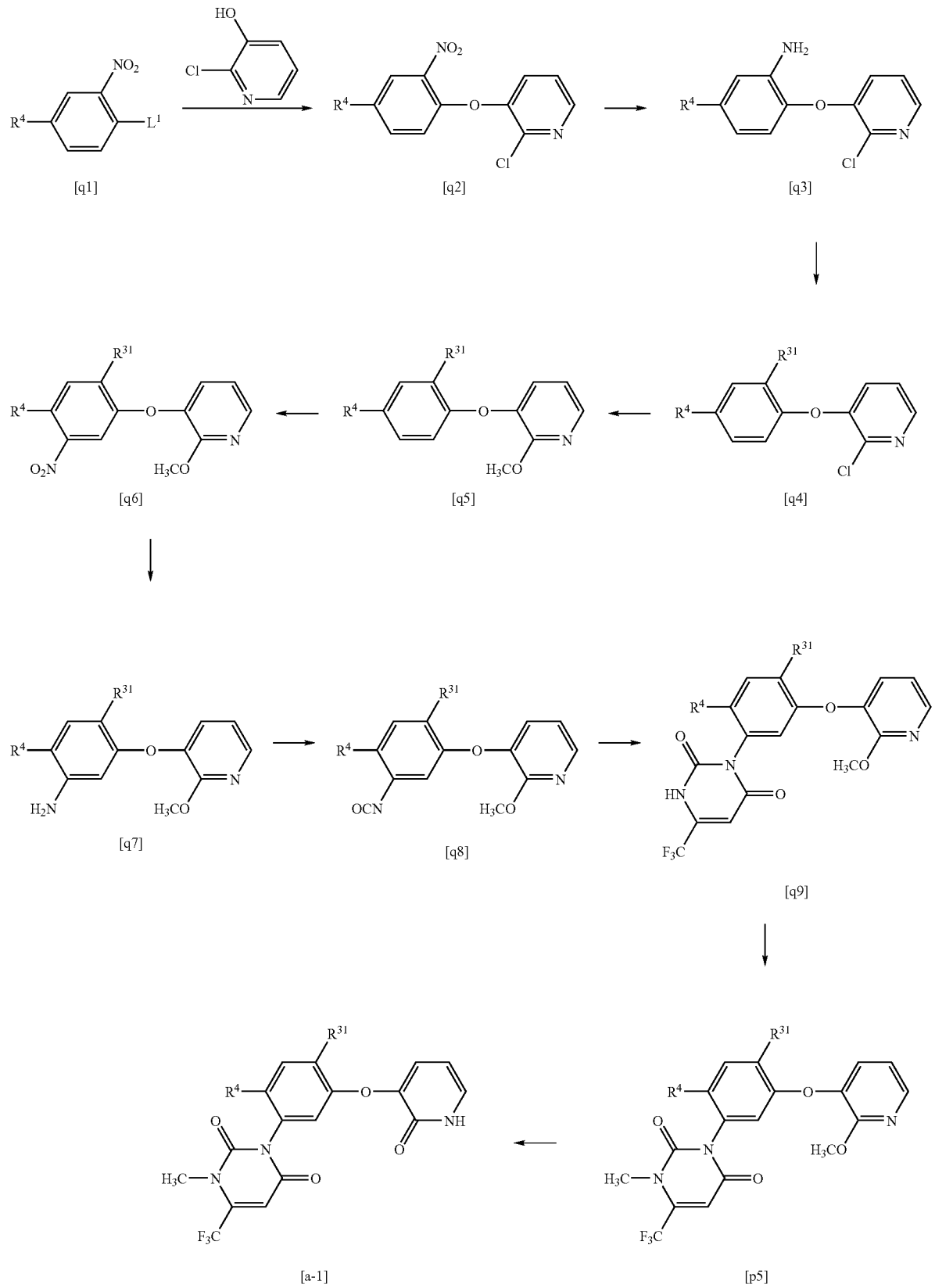

[wherein R⁴, R³¹ and L¹ represent the same meanings as defined above]

Compound [q1]→Compound [q2]

Compound [q2] can be prepared by making Compound [q1] react with 2-chloro-3-hydroxypyridine in the presence of a base such as potassium carbonate and so on usually in a solvent.

Compound [q2]→Compound [q3]

Compound [q3] can be prepared by making Compound [q2] react under hydrogen atmosphere in the presence of a catalyst such as palladium/carbon and so on usually in a solvent, or react with iron powder in a mixed solvent of acetic acid with water.

Compound [q3]→Compound [q4]

Compound [q4] can be prepared by making Compound [q3] react with a diazotizing agent such as sodium nitrite and so on and then copper chloride, copper bromide or copper cyanide in a solvent.

Compound [q4]→Compound [q5]

Compound [q5] can be prepared by making Compound [q4] react with methanol in the presence of a base usually in a solvent.

Compound [q5]→Compound [q6]

Compound [q6] can be prepared by making Compound [q5] react with nitric acid in sulfuric acid.

Compound [q6]→Compound [q7]

Compound [q7] can be prepared by making Compound [q6] react under hydrogen atmosphere in the presence of a catalyst such as palladium/carbon and so on usually in a solvent, or react with iron powder in a mixed solvent of acetic acid with water.

Compound [q7]→Compound [q8]

Compound [q8] can be prepared by making Compound [q7] react with phosgene usually in a solvent.

Compound [q8]→Compound [q9]

Compound [q9] can be prepared by making Compound [q8] react with ethyl 4,4,4-trifluoro-3-aminocrotonate in the presence of a base such as sodium hydride and so on usually in a solvent.

Compound [q9]→Compound [q5]

Compound [q5] can be prepared by making Compound [q9] react with a methylating agent such as dimethyl sulfate, methyl iodide and so on in the presence of a base such as sodium hydride and so on usually in a solvent.

Compound [p5]→Compound [a-1]

The pyridone compound [a-1], which is a pyridone compound [a] wherein R³ is a halogen atom or cyano group, can be prepared by making Compound [p5] react with boron tribromide usually in the presence of a solvent.

The pyridone compound [a] is also a compound having herbicidal activity and it is useful as an active ingredient of herbicide.

The pyridine compound [e]:

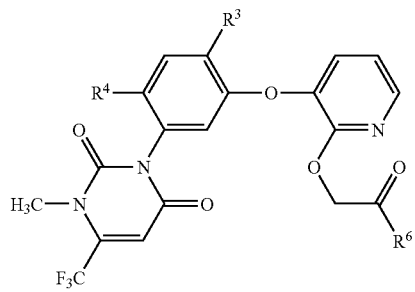

[e]

[wherein R³ and R⁴ represent the same meanings as defined above; R⁶ represents a C1–C6 haloalkoxy group, C3–C6 alkenyloxy group, C3–C6 haloalkenyloxy group, C3–C6 alkynyloxy group, C3–C6 haloalkynyloxy group, C3–C8 cycloalkoxy group, C3–C8 halocycloalkoxy group, C3–C8 cycloalkenyloxy group, C3–C8 cycloalkenyloxy group, C3–C8 halocycloalkenyloxy group, C1–C6 alkoxycarbonyl C1–C6 alkoxy group, C1–C6 alkylideneaminooxy group, C1–C6 alkylaminooxy group, (C1–C6 alkyl)(C1–3 alkyl) aminooxy group, optionally substituted phenoxy group, optionally substituted phenyl C1–C4 alkoxy group, amino group, C1–C6 alkoxyamino group, (C1–C6 alkoxy)(C1–3 alkyl)amino group, C1–C6 alkylamino group, (C1–C6 alkyl) C1–C6 alkylamino group, optionally substituted phenylamino group or optionally substituted phenyl C1–C4 alkylamino group], that is easily derived from the pyridine compound [d], is a compound having excellent herbicidal activity as well as the pyridine compound [d]. The pyridine compound [e] can be prepared by 1) a reaction of the pyridine compound [d] with Compound [z]:

$$H-R^6 \qquad [z]$$

[wherein R⁶ represents the same meaning as defined above] or 2) hydrolyzing the pyridine compound [d], deriving to its acid halide compound with a halogenating agent and then making the product react with Compound [z].

From the view of the herbicidal activity, in the pyridine compound [d] and the pyridine compound [e], preferable is a halogen atom for the group given by R³, especially chlorine atom among them, and preferable is a halogen atom for the group given by R⁴, especially fluorine atom among them.

The pyridine compound [d], the pyridine compound [e] and the pyridone compound [a] have excellent herbicidal activity, and some of them exhibit high selectivity between crops and weeds. The pyridine compound [d], the pyridine compound [e] and the pyridone compound [a] have herbicidal activity against the various troublesome weeds listed below in both foliar treatment and soil treatment in upland field.

Onagraceae weeds (eveningprimroses): *Oenothera erythrosepala* and *Oenothera laciniata*;

Ranunculaceae weeds (buttercups): *Ranunculus muricatus* and *Ranunculus sardous*;

Polygonaceae weeds (buckwheats): *Polygonum convolvulus* (wild buckwheat), *Polygonum lapathifolium* (pale smartweed), *Polygonum pensylvanicum* (Pensylvania smartweed), *Polygonum persicaria* (ladysthumb), *Rumex crispus* (curly cock), *Rumex obtusifolius* and *Polygonum cuspidatum* (Japanese knotweed);

Portulacaceae weeds (purslanes): *Portulaca oleracea* (common purslane);

Caryophyllaceae weeds (pinks): *Stellaria media* (common chickweed) and *Cerastium glomeratum* (sticky chickweed);

Chenopodiaceae weeds (goosefoots): *Chenopodium album* (common lambsquarters) and *Kochia scoparia* (mock cypress);

Amaranthaceae weeds (amaranths): *Amaranthus retroflexus* (redroot pigweed) and *Amaranthus hybridus*;

Crusiferae weeds (crusifers): *Raphanus raphanistrum* (wild radish), *Sinapis arvensis* (wild mustard), *Capsella bursapastoris* (shepherdspurse) and *Lepidium virginicum*;

Leguminosae weeds (beans): *Sesbania exaltata* (hemp sesbania), *Cassia obtusifolia* (sicklepod), *Desmodium tor-

*tuosum* (Florida beggarweed), *Trifolium repens* (white clover), *Vicia sativa* (common vetch) and *Medicago lupulina* (black medick);

Malvaceae weeds (mallows): *Abutilon theophrasti* (velvetleaf) and *Sida spinosa* (prickly *sida*);

Violaceae weeds (violets): *Viola arvensis* (field pansy) and *Viola tricolor* (wild pansy);

Rubiaceae weeds (bedstraws): *Galium aparine* (cleavers);

Convolvulaceae weeds (morning glories): *Ipomoea hederacea* (ivyleaf morning glory), *Ipomoea purpurea* (tall morning glory), *Ipomoea hederacea var integriuscula, Ipomoea lacunose* and *Convolvulus arvensis* (field bindweed); Labiatae weeds (mints): *Lamium purpureum* (purple deadnettle) and *Lamium amplexicaule* (henbit);

Solanaceae weeds (nightshades): *Datura stramonium* (jimsonweed) and *Solanum nigrum* (black nightshade);

Scrophulariaceae weeds (figworts): *Veronica persica* (Persian speedwell), *Veronica arvensis* and *Veronica hederaefolia* (ivyleaf speedwell);

Compositae weeds (composites): *Xanthium pensylvanicum* (common cocklebur), *Helianthus annuus* (common sunflower), *Matricaria chamomilla, Matricaria perforate orinodora* (scentless chamomile), *Chrysanthemum segetum* (corn marigold), *Matricaria matricarioides* (pineappleweed), *Ambrosia artemisiifolia* (common ragweed), *Ambrosia trifida* (giant ragweed), *Erigeron canadensis, Artemisia princeps* (Japanese mugwort), *Selidago altissima* and *Taraxacum officinala;*

Boraginaceae weeds (borages): *Myosotis arvensis* (field forget-me-not);

Asclepiadaceae weeds (waterplantains): *Asclepias syriaca* (common milkweed);

Euphorbiaceae weeds (spurges): *Euphorbia helioscopia* (sun spurge) and *Euphorhia maculate* (spotted spurge);

Geraniaceae weeds (geraniums): *Geranium carolinianum* (Carolina geranium);

Oxalidaceae weeds (woodsorrels): *Oxalis corymhosa* (creeping woodsorrel);

Cucurbitaceae weeds (gourds): *Sicyos angulatus;*

Gramineae weeds (grasses): *Echinochloa crus-galli*(barnyardgrass), *Setaria viridis* (green foxtail), *Setaria faberi* (giant foxtail), *Digitaris sanguinalis* (large crabgrass), *Eleusine indica* (goosegrass), *Poa annua* (annual bluegrass), *Alopecurus myosuroides* (blackgrass), *Avena fatua* (wild oat), *Sorghum halepense* (Johnsongrass), *Agropyron repens* (quackgrass), *Bromus tectorum* (downy brome), *Cynodone dactylon* (Bermudagrass), *Panicum dichotomiflorum* (fall *panicum*), *Panicum texanum* (Texas millet), *Sorghum vulgare* (shuttercane) and *Alopecurus geniculatus* (water foxtail);

Commelinaceae weeds (spiderworts): *Commelina communis* (Asiatic dayflower);

Equisetaceae weeds (horsetails): *Equisetum arvense* (field horsetail); and

Cyperaceae weeds (sedges): *Cyperus iria* (rice flatsedge), *Cyperus rotundus* (purple nutsedge) and *Cyperus esculentus* (yellow nutsedge).

Furthermore, some of the pyridine compound [d] and the pyridine compound [a] give no phytotoxicity to the main crops including maize (*Zea mays*), wheat (*Triticum aestivum*), barley (*Hordeum vulgare*), rice (*Oryza sativa*), sorghum (*Sorghum bicolor*), soybean (*Glycine max*), cotton (*Gossypium* spp.), sugar beat (*Beta vulgaris*), peanut (*Arachis hypogaea*), sunflower (*Helianthus annuus*), rape (*Brassica napus*) and so on; and horticultural plants including flowers, vegetables and so on. Furthermore, the pyridine compound [d], the pyridine compound [e] and the pyridone compound [a] are effectively used for controlling various troublesome weeds in no-tillage cultivation of soybean, maize, wheat and so on, and some of the pyridine compound [d], the pyridine compound [e] and the pyridone compound [a] exhibit no phytotoxicity on the crops.

The pyridine compound [d], the pyridine compound [e] and the pyridone compound [a] also have herbicidal activity against the various troublesome weeds listed below in the flooded treatment on paddy field.

Gramineae weeds (grasses): *Echinochloa oryzicola* (barnyardgrass),

Scrophulariaceae (figworts): *Lindernia procumbens* (common falsepimpernel);

Lythraceae (loothsterifes): *Rotala indica* (Indian toothcup) and *Ammannia multiflora;*

Elatinaceae (waterworts): *Elatine triandra* (waterwort);

Cyperaceae (sedges): *Cyperus difformis* (umbrella sedge), *Scirpus juncoides* (hardstem bulrush), *Eleocharis acicularis* (needle spikerush), *Cyperus serotinus* (water nutsedges) and *Eleocharis kuroguwai* (water chestnut);

Pontederiaceae (waterhyacinths): *Monochoria vaginalis;*

Alismataceae (waterplantains): *Sagittaria pygmaea* (arrowhead), *Sagittaria trifolia* and *Alisma canaliculatum* (waterplantain);

Potamogetonaceae (pondweeds): *Potamogeton distinctus* (roundleaf pondweed); and Umbelliferae (umbellifers): *Oenanthe javanica* (watercelery).

Some of the pyridine compound [d], the pyridine compound [e] and the pyridone compound [a] also exhibit no significant phytotoxicity on transplanted paddy rice.

Further, the pyridine compound [d], the pyridine compound [e] and the pyridone compound [a] can attain the control of weeds which are growing or will grow in the non-cultivated lands such as embankments; riverbanks; roadsides; railways; green tracts of parks; grounds; parking places; airports; industrial facilities including factories, warehouses and so on; unused farms and unused lands in the city; and in the orchards, grasslands, lawns and forests. The pyridine compound [d], the pyridine compound [e] and the pyridone compound [a] also have herbicidal activity against aquatic weeds, such as *Eichhornia crassipes* (water hyacinth) and so on, which are growing or will grow in the rivers, waterways, canals, ponds and so on.

The pyridine compound [d], the pyridine compound [e] and the pyridone compound [a]have the same properties as those of the herbicidal compounds described in the international patent publication WO95/34659. In the case of cultivating crops wherein tolerance is bestowed to the said crops by introducing a herbicidal tolerance gene described in the said specification, the pyridine compound [d], the pyridine compound [e] and the pyridone compound [a] can be used at larger amounts than those used when ordinary crops without tolerance are cultivated, thus making it possible to control other unfavorable weeds more effectively.

When the pyridine compound [d], the pyridine compound [e] or the pyridone compound [a] is used as the active ingredient of a herbicide, it is usually mixed with solid or liquid carriers, surfactants, and other auxiliary agents to give emulsifiable concentrates, wettable powders, suspensible concentrates, granules, concentrated emulsions, water dispersible granules and so on.

These formulations may comprise the pyridine compound [d], the pyridine compound [e] or the pyridone compound [a] as an active ingredient at an amount from 0.001 to 80%, preferably from 0.005 to 70% by weight.

The solid carrier may include, for example, mineral fine powders such as kaolin clay, attapulgite clay, bentonite, acid clay, pyrophyllite, talc, diatomaceous earth, calcite and so on; organic fine powders such as walnut shell powder and so on; water-soluble organic fine powders such as urea and so on; inorganic salt fine powders such as ammonium sulfate and so on; and fine powders of synthetic hydrated silicon oxide. The liquid carrier may include, for example, aromatic hydrocarbons such as methylnaphthalene, phenylxylylethane, alkylbenzene (e.g., xylene) and so on; alcohols such as isopropanol, ethylene glycol, 2-ethoxyethanol and so on; esters such as dialkyl phthalate and so on; ketones such as acetone, cyclohexanone, isophorone and so on; mineral oils such as machine oil and so on; vegetable oils such as soybean oil, cottonseed oil and so on; dimethyl sulfoxide; N,N-dimethylformamide; acetonitrile; N-methylpyrrolidone; water; and so on.

As the surfactant used for emulsifying, dispersing or spreading, anionic surfactants such as alkylsulfate salts, alkylsulfonate salts, alkylarylsulfonate salts, dialkylsulfosuccinate salts, polyoxyethylenealkyl aryl ether phosphate salts and so on; and nonionic surfactants such as polyoxyethylenealkyl ethers, polyoxyethylenealkyl aryl ethers, polyoxyethylene polyoxypropylene block copolymers, sorbitan fatty acids, polyoxyethylene sorbitan fatty acid esters and so on.

Ligninsulfonic acid salts, alginic acid salts, plyvinyl alcohol, gum arabic, CMC (carboxymethylcellulose), PAP (isopropyl acid phosphate) and so on are set forth as the other auxiliary agents.

The pyridine compound [d], the pyridine compound [e] or the pyridone compound [a] is usually formulated and then used for soil treatment, foliar treatment or flooded treatment before or after the emergence of weeds. The soil treatment may include soil surface treatment and soil incorporation treatment. Further, foliar treatment may include application over the plants and directed application in which it is applied only to weeds so as to keep off the crop plants.

Furthermore, by intermixing other herbicides, there are situations wherein an enhanced the herbicidal efficacy is confirmed.

In the case when the pyridine compound [d], the pyridine compound [e] or the pyridone compound [a] is utilized as an active ingredient of a herbicide, the application dosage may vary with the weather conditions, formulation types, application timing, application methods, soil conditions, objective crops and objective weeds, but is usually 0.01 g to 20000 g, preferably 1 g to 12000 g per one hectare. When emulsifiable concentrates, wettable powders, suspensible concentrates, concentrated emulsions, water dispersible granules and so on are applied, they are applied by diluting usually in 10 liters to 1000 liters of water (if necessary, the water may include an adjuvant such as a spreading agent) so the designated amount can be applied to each hectare. Granules and some types of flowables are usually applied without dilution. The adjuvant which can be used herein, if necessary, may include, in addition to the surfactants described above, polyoxyethylene resin acids (esters), ligninsulfonic acid salts, abietic acid salts, dinaphthylmethanedisulfonic acid salts, crop oil concentrate, vegetable oils such as soybean oil, corn oil, cottonseed oil, sunflower oil and so on.

Hereinafter, the present invention is explained more detailedly by examples and reference examples, but the said examples do not limit the present invention in any way.

EXAMPLE 1

To a mixture of 0.5 g of 3-[2-chloro-4-fluoro-5-(3-methyl-2,6-dioxo-4-trifluoromethyl-1,2,3,6-tetrahydropyrimidin-1-yl)phenoxy]-1H-pyridin-2-one:

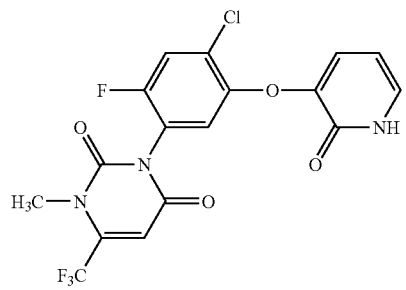

and 8 mg of rhodium (II) trifluoroacetate dimer and 15 ml of dichloroethane, 0.15 g of methyl diazoacetate was dropped at 80° C. over 3 hours. After dropping, the reaction mixture was further stirred for one hour at 80° C., and then concentrated. The residue was subjected to silica gel column chromatography (eluent; hexane/ethyl acetate=3/1 to 0/1) to give 0.18 g of recovered 3-[2-chloro-4-fluoro-5-(3-methyl-2,6-dioxo-4-trifluoromethyl-1,2,3,6-tetrahydropyrimidin-1-yl)phenoxy]-1H-pyridin-2-one and 0.34 g of 3-[2-chloro-4-fluoro-5-(3-methyl-2,6-dioxo-4-trifluoromethyl-1,2,3,6-tetrahydropyrimidin-1-yl)phenoxy]-2-(methoxycarbonylmethoxy)pyridine:

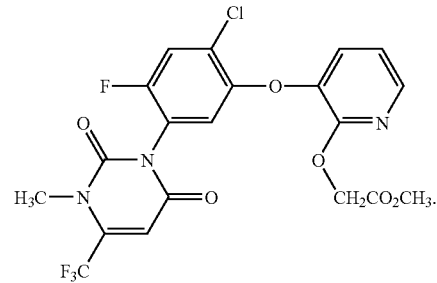

Mp. 52.2° C.
$^1$H-NMR (300M Hz, CDCl$_3$, TMS δ (ppm)): 3.50 (3H, q, J=1.0 Hz), 3.70 (3H, s), 4.90 (1H, d, J=15.8 Hz), 4.97 (1H, d, J=15.8 Hz), 6.29 (1H, s), 6.90–6.95 (2H, m), 7.32 (1H, dd, J=1.9 Hz, 7.7 Hz), 7.37 (1H, d, J=8.7 Hz), 7.92 (1H, dd, J=1.9 Hz, 4.9 Hz)

EXAMPLE 2

Into a mixture of 1.0 g of 3-[2-chloro-4-fluoro-5-(3-methyl-2,6-dioxo-4-trifluoromethyl-1,2,3,6-tetrahydropyrimidin-1-yl)phenoxy]-1H-pyridin-2-one, 42 µl of boron trifluoride-diethyl ether complex and 40 ml of 1,2-dichloroethane, 0.4 ml of ethyl diazoacetate (purity: 90%) was dropped at room temperature over 2 hours. After dropping, the reaction mixture was further stirred for two hours, and then subjected to silica gel column chromatography (eluent; hexane/ethyl acetate=2/1) to give 1.10 g of 3-[2-chloro-4-fluoro-5-(3-methyl-2,6-dioxo-4-trifluoromethyl-1,2,3,6-tetrahydropyrimidin-1-yl)phenoxy]-2-(ethoxycarbonylmethoxy)pyridine:

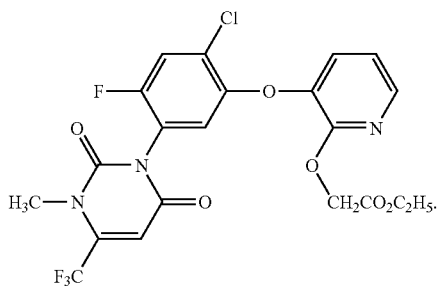

$^1$H-NMR (300 MHz, CDCl$_3$, TMS δ (ppm)): 1.25 (3H, t, J=7.1 Hz), 3.50 (3H, q, J=1.2 Hz), 4.16 (2H, q, J=7.1 Hz), 4.88 (1H, d, J=15.9 Hz), 4.96 (1H, d, J=15. 9 Hz), 6.29 (1H, s), 6.9–7.0 (2H, m), 7.3–7.4 (2H, m), 7.9–8.0 (1H, m)

The N-alkylated compound, 3-[2-chloro-4-fluoro-5-(3-methyl-2,6-dioxo-4-trifluoromethyl-1,2,3,6-tetrahydropyrimidin-1-yl)phenoxy]-1-(ethoxycarbonylmethoxy)-1H-pyridin-2-one was not detected.

Analysis Condition:
High pressure liquid chromatography
Liquid chromatograph LC-10AS (manufactured by Shimadzu Corp.)
Detector: UV-Vis detector SPD-10A (manufactured by Shimadzu Corp.)
Detected wave length: 254 nm
Column: SUMIPAX ODS A-212 (manufactured by Sumika Chemical Analysis Service)
Column temperature: Room temperature
Moving bed: acetonitrile/water=1/1

EXAMPLE 3

The First Step

Into a mixture of 1.01 g of ethyl glicinate hydrochloride, 1.83 g of water and 5.15 g of 1,2-dichloroethane, a solution of 0.60 g of sodium nitrite in 1.82 g of water was dropped at about −5° C. After dropping, the reaction mixture was further stirred for 1.5 hours at the same temperature, 0.67 g of 5% sulfuric acid was added dropwise therein, and then further stirred for 10 minutes. Then, the separated organic layer was washed with 5% aqueous sodium bicarbonate solution and dried over anhydrous magnesium sulfate to give a 1,2-dichloroethane solution of ethyl diazoacetate.

The Second Step

Into a mixture of 1.8 g of 3-[2-chloro-4-fluoro-5-(3-methyl-2,6-dioxo-4-trifluoromethyl-1,2,3,6-tetrahydropyrimidin-1-yl)phenoxy]-1H-pyridin-2-one, 0.026 g of boron trifluoride-diethyl ether complex and 6 ml of 1,2-dichloroethane, the 1,2-dichloroethane solution of ethyl diazoacetate obtained by the first step was dropped at room temperature over 30 minutes. After dropping, the reaction mixture was further stirred for 1.5 hours, 2 ml of 15% sulfuric acid was added dropwise therein, and then further stirred for 30 minutes. Twenty milliliters (20 ml) of aqueous saturated sodium bicarbonate solution were added to the reaction mixture and the separated organic layer was dried over anhydrous magnesium sulfate and concentrated. The residue was subjected to silica gel column chromatography (eluent; hexane/ethyl acetate=2/1) to give 1.94 g of 3-[2-chloro-4-fluoro-5-(3-methyl-2,6-dioxo-4trifluoromethyl-1,2,3,6-tetrahydropyrimidin-1-yl)phenoxy]-2-(ethoxycarbonylmethoxy)pyridine.

EXAMPLE 4

Into a mixture of 1.0 g of 3-[2-chloro-4-fluoro-5-(3-methyl-2,6-dioxo-4-trifluoromethyl-1,2,3,6-tetrahydropyrimidin-1-yl)phenoxy]-1H-pyridin-2-one, 121 mg of tin tetrachloride and 40 ml of 1,2-dichloroethane, 0.4 ml of ethyl diazoacetate (purity: 90%) is dropped at room temperature over 2 hours. After dropping, the reaction mixture is further stirred for 2 hours, and subjected to silica gel column chromatography (eluent; hexane/ethyl acetate=2/1) to give 3-[2-chloro-4-fluoro-5-(3-methyl-2,6-dioxo-4-trifluoromethyl-1,2,3,6-tetrahydropyrimidin-1-yl)phenoxy]-2-(ethoxycarbonylmethoxy)pyridine.

EXAMPLE 5

Into a mixture of 1.0 g of 3-[2-chloro-4-fluoro-5-(3-methyl-2,6-dioxo-4-trifluoromethyl-1,2,3,6-tetrahydropyrimidin-1-yl)phenoxy]-1H-pyridin-2-one, 70 mg of trifluoromethanesulfonic acid and 40 ml of 1,2-dichloroethane, 0.4 ml of ethyl diazoacetate (purity: 90%) is dropped at room temperature over 2 hours. After dropping, the reaction mixture is further stirred for 2 hours, and subjected to silica gel column chromatography (eluent; hexane/ethyl acetate=2/1) to give 3-[2-chloro-4-fluoro-5-(3-methyl-2,6-dioxo-4-trifluoromethyl-1,2,3,6-tetrahydropyrimidin-1-yl)phenoxy]-2-(ethoxycarbonylmethoxy)pyridine.

Next, reference examples are described for the preparation of the starting materials and so on.

REFERENCE EXAMPLE 1

The First Step

To a mixture of 20.0 g of 2-chloro-4-fluoro-5-(3-methyl-2,6-dioxo-4-trifluoromethyl-1,2,3,6-tetrahydropyrimidin-1-yl)phenol, 10.8 g of dimethyl chloromalonate and 120 ml of N,N-dimethylformamide, 9.79 g of potassium carbonate were added and stirred at 70° C. for 1.5 hours. After the reaction mixture was cooled to room temperature, it was poured into a mixture of hydrochloric acid and ice and extracted with ethyl acetate. The organic layer was washed with 10% aqueous potassium carbonate solution and saturated brine subsequently, dried over anhydrous magnesium sulfate and concentrated. The residue was washed with methanol and diisopropyl ether to give 21.6 g of dimethyl [2-chloro-4-fluoro-5-(3-methyl-2,6-dioxo-4-trifluoromethyl-1,2,3,6-tetrahydropyrimidin-1-yl)phenoxy]malonate.
Mp. 141.1° C.
$^1$H-NMR (300M Hz, CDCl$_3$, TMS δ (ppm)): 3.55 (d, 3H, J=1.1 Hz), 3.86 (s, 6H), 5.15 (s, 1H), 6.35 (s, 1H), 6.99 (d, 1H, J=6.5 Hz), 7.3–7.4 (m, 1H)

The Second Step

Into a mixture of 21.6 g of dimethyl [2-chloro-4-fluoro-5-(3-methyl-2,6-dioxo-4-trifluoromethyl-1,2,3,6-tetrahydropyrimidin-1-yl)phenoxy] malonate, 80 ml of chloroform and 80 ml of methanol, 26.3 ml of 7N-ammonia/methanol solution were dropped at 0° C. After dropping, the reaction mixture was stirred for 20 minutes, and further 7 hours at room temperature. The reaction mixture was filtered and concentrated to give 6.91 g of methyl 2-[2-chloro-4-fluoro-5-(3-methyl-2,6-dioxo-4-trifluoromethyl-1,2,3,6-tetrahydropyrimidin-1-yl)phenoxy]-2-carboxamideacetate.
Mp. 196.4° C. (decomp.)
$^1$H-NMR (250M Hz, CDCl$_3$, TMS δ (ppm): 3.56 (s, 3H), 3.84 (s, 3H), 5.06 (s, 1H), 5.76 (bs, 1H), 6.36 (s, 1H), 6.8–7.0 (m, 2H), 7.37 (d, 1H, J=8.7 Hz)

The Third Step

To a mixture of 363 mg of methyl 2-[2-chloro-4-fluoro-5-(3-methyl-2,6-dioxo-4-trifluoromethyl-1,2,3,6-tetrahydropyrimidin-1-yl)phenoxy]-2-carboxyamideacetate, 6.0 ml of tetrahydrofuran and 50 mg of acrolein, 9 mg of potassium t-butoxide were added at 0° C. and stirred for 30 minutes. Then, after 17 mg of p-toluenesulfonic acid monohydrate were added to the reaction mixture, the mixture was refluxed with stirring for one hour. The reaction mixture was cooled to room temperature, and then water was poured therein and the mixture was extracted with ethyl acetate. The organic layer was dried over anhydrous magnesium sulfate and concentrated. The residue was subjected to silica gel column chromatography to give 202 mg of 3-[2-chloro-4-fluoro-5-(3-methyl-2,6-dioxo-4-trifluoromethyl-1,2,3,6-tetrahydropyrimidin-1-yl)phenoxy]-3-methoxycarbonyl-3,4-dihydro-1H-pyridin-2-one.

Mp. 82.4° C.

The Fourth Step

A mixture of 202 mg of 3-[2-chloro-4-fluoro-5-(3-methyl-2,6-dioxo-4-trifluoromethyl-1,2,3,6-tetrahydropyrimidin-1-yl)phenoxy]-3-methoxycarbonyl-3,4-dihydro-1H-pyridin-2-one, 52 mg of lithium chloride, 2 ml of dimethyl sulfoxide and 10 μl of water was stirred at 120° C. for one hour. The reaction mixture was cooled to room temperature, and then water was poured therein and the mixture was extracted with ethyl acetate. The organic layer was washed with saturated brine, dried over anhydrous magnesium sulfate and concentrated. The residue was subjected to silica gel column chromatography to give 70 mg of 3-[2-chloro-4-fluoro-5-(3-methyl-2,6-dioxo-4-trifluoromethyl-1,2,3,6-tetrahydropyrimidin-1-yl)phenoxy]-3,4-dihydro-1H-pyridin-2-one.

Mp. 91.0° C.

$^1$H-NMR (300M Hz, CDCl$_3$, TMS δ (ppm): 2.7–2.8 (m, 2H), 3.53 (s, 3H), 4.6–4.8 (m, 1H), 5.0–5.2 (m, 1H), 6.0–6.1 (m, 1H), 6.33 (s, 1H), 7.1–7.2 (m, 1H), 7.28 (d, 1H, J=9.0 Hz), 7.7–8.1 (m, 1H)

The Fifth Step

A mixture of 144 mg of 3-[2-chloro-4-fluoro-5-(3-methyl-2,6-dioxo-4-trifluoromethyl-1,2,3,6-tetrahydropyrimidin-1-yl)phenoxy]-3,4-dihydro-1H-pyridin-2-one, 0.66 ml of tetrahydrofuran and 163 mg of o-chloranil was refluxed with stirring for one hour. The reaction mixture was cooled to room temperature, and then water was poured therein and the mixture was extracted with ethyl acetate. The organic layer was dried over anhydrous magnesium sulfate and concentrated. The residue was subjected to silica gel column chromatography to give 72 mg of 3-[2-chloro-4-fluoro-5-(3-methyl-2,6-dioxo-4-trifluoromethyl-1,2,3,6-tetrahydropyrimidin-1-yl)phenoxy]-1H-pyridin-2-one.

$^1$H-NMR (300M Hz, CDCl$_3$, TMS δ (ppm)) δ 3.52 (s, 3H), 6.22 (dd, 1H, J=7.0, 7.0 Hz), 6.32 (s, 1H), 6.95 (d, 1H, J=6.6 Hz), 7.00 (dd, 1H, J=7.0, 1.6 Hz), 7.2–7.3 (m, 1H), 7.39 (d, 1H, J=8.9 Hz)

REFERENCE EXAMPLE 2

The First Step

To a mixture of 1.3 g of sodium hydride and 100 ml of dimethoxyethane, 10 g of 2-chloro-4-fluoro-5-(3-methyl-2,6-dioxo-4-trifluoromethyl-1,2,3,6-tetrahydropyrimidin-1-yl)phenol were added at room temperature and stirred for 30 minutes. Then, 2.2 g of sodium iodide and 6.7 g of crude 2-chloro-2-(methylthio)acetamide were added thereto and stirred at room temperature for 3 hours, and water was poured into the reaction mixture. The reaction mixture was extracted with ethyl acetate. The organic layer was washed with aqueous sodium bicarbonate solution, dried over anhydrous magnesium sulfate and concentrated. The residue was subjected to silica gel column chromatography (eluent: ethyl acetate) to give 10.2 g of 2-[2-chloro-4-fluoro-5-(3-methyl-2,6-dioxo-4-trifluoromethyl-1,2,3,6-tetrahydropyrimidin-1-yl)phenoxy]-2-(methylthio) acetamide.

$^1$H-NMR (CDCl$_3$, 300M Hz, TMS δ (ppm): 2.18 (3H, s), 3.56 (3H, q, J=1.3 Hz), 5.54 (1H, d, J=3.4 Hz), 5.94 (1H, br), 6.37 (1H, d, J=2.9 Hz), 6.80 (1H, br), 7.06–7.11 (1H, m), 7.36 (1H, d, J=9.0 Hz)

The Second Step

To a mixture of 2-[2-chloro-4-fluoro-5-(3-methyl-2,6-dioxo-4-trifluoromethyl-1,2,3,6-tetrahydropyrimidin-1-yl)phenoxy]-2-(methylthio)acetamide and 50 ml of chloroform, 3.7 g of m-chloroperbenzoic acid were added and stirred at room temperature for 3 days. To the reaction mixture, aqueous sodium bicarbonate solution and aqueous sodium thiosulfate solution were added. The reaction mixture was extracted with ethyl acetate. The organic layer was washed with saturated brine, dried over anhydrous magnesium sulfate and concentrated. The residue was subjected to silica gel column chromatography (eluent: ethyl acetate) to give 3.3 g of 2-[2-chloro-4-fluoro-5-(3-methyl-2,6-dioxo-4-trifluoromethyl-1,2,3,6-tetrahydropyrimidin-1-yl)phenoxy]-2-(methylsulfonyl)acetamide.

$^1$H-NMR (300M Hz, CDCl$_3$, TMS δ (ppm): 3.11 (3H, s), 3.46 (1.5H, s), 3.49 (1.5H, s), 5.44 (1H, s), 6.26 (0.5H, s), 6.30 (0.5H, s), 6.55 (1H, br), 7.03 (1H, br), 7.27–7.34 (2H, m)

The Third Step

To a mixture of 1.3 g of 2-[2-chloro-4-fluoro-5-(3-methyl-2,6-dioxo-4-trifluoromethyl-1,2,3,6-tetrahydropyrimidin-1-yl)phenoxy]-2-(methylsulfonyl) acetamide, 0.21 g of acrolein and 20 ml of THF, 0.03 g of potassium t-butoxide was added at room temperature, and stirred for 3.5 hours. Then, 0.1 g of p-toluenesulsonic acid was added and the reaction mixture was refluxed under stirring for 4 hours. The reaction liquid was concentrated under reduced pressure and the residue was subjected to silica gel column chromatography (eluent: hexane/ethyl acetate=1/1) to give 0.55 g of 3-[2-chloro-4-fluoro-5-(3-methyl-2,6-dioxo-4-trifluoromethyl-1,2,3,6-tetrahydropyrimidin-1-yl)phenoxy]-3-(methylsulfonyl)-3,4-dihydro-1H-pyridin-2-one.

$^1$H-NMR (300M Hz, CDCl$_3$, TMS δ (ppm): 2.75–2.88 (1H, m), 3.19–3.31 (1H, m), 3.30 (1H, s), 3.54 (3H, s), 4.97–5.05 (1H, m), 6.00–6.05 (1H, m), 7.27–7.36 (2H, m), 8.04 (1H, d, J=4.1 Hz)

Fourth Step

A mixture of one equivalent of 3-[2-chloro-4-fluoro-5-(3-methyl-2,6-dioxo-4-trifluoromethyl-1,2,3,6-tetrahydropyrimidin-1-yl)phenoxy]-3-(methylsulfonyl)-3,4-dihydro-1H-pyridin-2-one, 0.1 equivalent of p-toluenesulfonic acid and toluene is refluxed under stirring. After the reaction, the reaction liquid is concentrated and the residue is subjected to silica gel column chromatography to give 3-[2-chloro-4-fluoro-5-(3-methyl-2,6-dioxo-4-trifluoromethyl-1,2,3,6-tetrahydropyrimidin-1-yl)phenoxy]-1H-pyridin-2-one.

REFERENCE EXAMPLE 3

The First Step

To 8.33 g of dimethyl chloromalonate, 10.7 ml of 7N ammonia/methanol solution was dropped at 0° C. and then stirred for 10 minutes. The reaction mixture was further stirred at room temperature for 2 hours, filtered and concentrated. The residue was dissolved with a mixed solvent of chloroform with methanol. The solution was filtered, and then concentrated. The residue was subjected to silica gel column chromatography to give 4.4 g of methyl 2-chloro-2-carboxamideacetate.

Mp. 79.5° C.

$^1$H-NMR (300 M Hz, CDCl$_3$, TMS δ (ppm)): 3.86 (s, 3H), 4.79 (s, 1H), 5.8–6.0 (bs, 1H), 6.5–6.7 (bs, 1H)

The Second Step

To a mixture of 0.50 g of 2-chloro-4-fluoro-5-(3-methyl-2,6-dioxo-4-trifluoromethyl-1,2,3,6-tetrahydropyrimidin-1-yl)phenol, 0.22 g of methyl 2-chloro-2-carboxamideacetate and 0.75 ml of N,N-dimethylformamide, 0.24 g of potassium carbonate was added and stirred at 50–60° C. for 0.5 hour. To the mixture, 0.75 ml of N,N-dimethylformamide was added and further stirred at 50–60° C. for 2 hours. The reaction mixture was cooled to room temperature and poured into ice. The precipitated crystals were filtered off and washed with water and hexane subsequently to give 0.42 g of methyl 2-[2-chloro-4-fluoro-5-(3-methyl-2,6-dioxo-4-trifluoromethyl-1,2,3,6-tetrahydropyrimidin-1-yl)phenoxy]-2-(carboxamide) acetate.

REFERENCE EXAMPLE 4

The First Step

To a mixture of 10 g of 3-(2,5-difluoro-4-nitrophenyl)-1-methyl-6-trifluoromethyl-1H-pyrimidin-2,4-dione, 5.0 g of 3-hydroxy-2-methoxypyridine and 100 ml of N,N-dimethylformamide, 7.8 g of potassium carbonate were added and refluxed for 6 hours under stirring. Then, the reaction mixture was poured into water and extracted with ethyl acetate. The organic layer was washed with aqueous sodium bicarbonate and saturated brine subsequently, dried over magnesium sulfate and concentrated to give 12.8 g of 3-[4-fluoro-5-(3-methyl-2,6-dioxo-4-trifluoromethyl-2-nitro-1,2,3,6-tetrahydropyrimidin-1-yl)phenoxy]-2-methoxypyridine.

$^1$H-NMR (300M Hz, CDCl$_3$, TMS δ (ppm)): 3.52 (3H, q, J=1.2 Hz), 3.93 (3H, s), 6.32 (1H, s), 6.76 (1H, d, J=5.8 Hz), 6.93 (1H, dd, J=5.0 Hz, 7.8 Hz), 7.40 (1H, dd, J=1.4 Hz, 7.8 Hz), 7.90 (1H, d, J=8.6 Hz), 8.04 (1H, dd, J=1.4 Hz, 5.0 Hz)

The Second Step

Into a mixture of 6.3 g of iron powder, 50 ml of acetic acid and 50 ml of water, 60 ml of an ethyl acetate solution of 3-[4-fluoro-5-(3-methyl-2,6-dioxo-4-trifluoromethyl-2-nitro-1,2,3,6-tetrahydropyrimidin-1-yl)phenoxy]-2-methoxypyridine were dropped at 80° C. After dropping, the reaction mixture was stirred for 15 minutes at the same temperature and cooled to room temperature. The reaction mixture was poured into water and extracted with ethyl acetate. The organic layer was washed with water, aqueous sodium bicarbonate and saturated brine subsequently, and concentrated to give 12.1 g of 3-[2-amino-4-fluoro-5-(3-methyl-2,6-dioxo-4-trifluoromethyl-1,2,3,6-tetrahydropyrimidin-1-yl)phenoxy]-2-methoxypyridine.

$^1$H-NMR (300M Hz, CDCl$_3$, TMS δ (ppm)): 3.51 (3H, q, J=1.0 Hz), 4.00 (3H, s), 4.20 (1H, br), 6.30 (1H, s), 6.62 (1H, d, J=10.6 Hz), 6.63 (1H, d, J=7.1 Hz), 6.82 (1H, dd, J=5.0 Hz, 7.8 Hz), 7.18 (1H, dd, J=1.4 Hz, 7.8 Hz), 7.90 (1H, dd, J=1.4 Hz, 5.0 Hz)

The Third Step

Into a mixture of 12 g of 3-[2-amino-4-fluoro-5-(3-methyl-2,6-dioxo-4-trifluoromethyl-1,2,3,6-tetrahydropyrimidin-1-yl)phenoxy]-2-methoxypyridine, 2.8 g of cuprous chloride, 5.7 g of cupric chloride and 100 ml of acetonitrile, 4.6 g of imsoanyl nitrite were dropped. After dropping, the reaction mixture was stirred for 2 hours and left for 2 days. Then, aqueous ammonia was added thereto and the mixture was extracted with ethyl acetate. The organic layer was washed with water and saturated brine subsequently, dried over anhydrous magnesium sulfate and concentrated. The residue was subjected to silica gel column chromatography (eluent: hexane/ethyl acetate=2/1) to give 8.6 g of 3-[2-chloro-4-fluoro-5-(3-methyl-2,6-dioxo-4-trifluoromethyl-1,2,3,6-tetrahydropyrimidin-1-yl)phenoxy]-2-methoxypyridine.

Mp. 179.5° C.

The Fourth Step

To a mixture of 0.5 g of 3-[2-chloro-4-fluoro-5-(3-methyl-2,6-dioxo-4-trifluoromethyl-1,2,3,6-tetrahydropyrimidin-1-yl)phenoxy]-2-methoxypyridine and 10 ml of chloroform, 0.5 g of boron tribromide was added and stirred at room temperature for 3 hours. Then the reaction mixture was concentrated. The residue was poured into water and extracted with ethyl acetate. The organic layer was dried over anhydrous magnesium sulfate and conventrated. The residue was subjected to silica gel column chromatography (eluent: ethyl acetate) to give 0.31 g of 3-[2-chloro-4-fluoro-5-(3-methyl-2,6-dioxo-4-trifluoromethyl-1,2,3,6-tetrahydropyrimidin-1-yl)phenoxy]-1H-pyridin-2-one.

Mp. 180.8° C.

Some of the pyridine compound [d] and pyridine compound [e] are listed with their compound numbers below.

Compounds given by the following formula:

TABLE 1

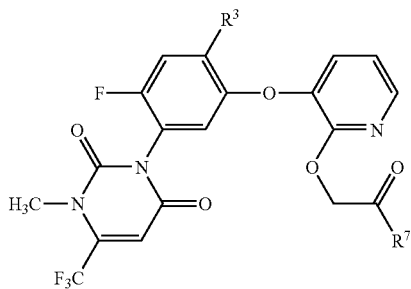

| Compound number | R$^3$ | R$^7$ |
|---|---|---|
| 1 | Cl | OH |
| 2 | Cl | OMe |
| 3 | Cl | OEt |
| 4 | Cl | Oi-Pr |
| 5 | Cl | OCH$_2$CH=CH$_2$ |
| 6 | Cl | OCH$_2$CH$_2$CH$_3$ |
| 7 | Cl | OCH$_2$CH$_2$CH$_2$CH$_3$ |
| 8 | Cl | OCH$_2$CH$_2$CH$_2$CH$_2$CH$_3$ |
| 9 | Cl | OC(CH$_3$)$_3$ |
| 10 | Cl | OCH$_2$C$_6$H$_5$ |
| 11 | Cl | OC$_6$H$_5$ |
| 12 | Cl | NHOCH$_3$ |
| 13 | Cl | NHOCH$_2$CH$_3$ |
| 14 | Cl | N(CH$_3$)OCH$_3$ |

TABLE 1-continued

[Structure: pyridone compound with F, O, N-CH3, F3C, and pyridine ring linked via O to -C(=O)-R7, with R3 on phenyl]

| Compound number | R³ | R⁷ |
| --- | --- | --- |
| 15 | Cl | ON=C(CH₃)₂ |
| 16 | Cl | OCH₂CO₂CH₃ |
| 17 | Cl | OCH(CH₃)CO₂CH₂CH₃ |
| 18 | Cl | OC(CH₃)₂CO₂CH₃ |
| 19 | Cl | Oc-C₅H₉ |
| 20 | Br | OH |
| 21 | Br | OMe |
| 22 | Br | OEt |
| 23 | Br | Oi-Pr |
| 24 | Br | OCH₂CH=CH₂ |
| 25 | Br | OCH₂CH₂CH₃ |
| 26 | Br | OCH₂CH₂CH₂CH₃ |
| 27 | Br | OCH₂CH₂CH₂CH₂CH₃ |
| 28 | Br | OC(CH₃)₃ |
| 29 | Br | OCH₂C₆H₅ |
| 30 | Br | OC₆H₅ |
| 31 | Br | NHOCH₃ |
| 32 | Br | NHOCH₂CH₃ |
| 33 | Br | N(CH₃)OCH₃ |
| 34 | Br | ON=C(CH₃)₂ |
| 35 | Br | OCH₂CO₂CH₃ |
| 36 | Br | OCH(CH₃)CO₂CH₂CH₃ |
| 37 | Br | OC(CH₃)₂CO₂CH₃ |
| 38 | Br | Oc-C₅H₉ |
| 39 | CN | OH |
| 40 | CN | OMe |
| 41 | CN | OEt |
| 42 | CN | Oi-Pr |
| 43 | CN | OCH₂CH=CH₂ |
| 44 | CN | OCH₂CH₂CH₃ |
| 45 | CN | OCH₂CH₂CH₂CH₃ |
| 46 | CN | OCH₂CH₂CH₂CH₂CH₃ |
| 47 | CN | OC(CH₃)₃ |
| 48 | CN | OCH₂C₆H₅ |
| 49 | CN | OC₆H₅ |
| 50 | CN | NHOCH₃ |
| 51 | CN | NHOCH₂CH₃ |
| 52 | CN | N(CH₃)OCH₃ |
| 53 | CN | ON=C(CH₃)₂ |
| 54 | CN | OCH₂CO₂CH₃ |
| 55 | CN | OCH(CH₃)CO₂CH₂CH₃ |
| 56 | CN | OC(CH₃)₂CO₂CH₃ |
| 57 | CN | Oc-C₅H₉ |
| 58 | NO₂ | OH |
| 59 | NO₂ | OMe |
| 60 | NO₂ | OEt |
| 61 | NO₂ | Oi-Pr |
| 62 | NO₂ | OCH₂CH=CH₂ |
| 63 | NO₂ | OCH₂CH₂CH₃ |
| 64 | NO₂ | OCH₂CH₂CH₂CH₃ |
| 65 | NO₂ | OCH₂CH₂CH₂CH₂CH₃ |
| 66 | NO₂ | OC(CH₃)₃ |
| 67 | NO₂ | OCH₂C₆H₅ |
| 68 | NO₂ | OC₆H₅ |
| 69 | NO₂ | NHOCH₃ |
| 70 | NO₂ | NHOCH₂CH₃ |
| 71 | NO₂ | N(CH₃)OCH₃ |
| 72 | NO₂ | ON=C(CH₃)₂ |
| 73 | NO₂ | OCH₂CO₂CH₃ |
| 74 | NO₂ | OCH(CH₃)CO₂CH₂CH₃ |
| 75 | NO₂ | OC(CH₃)₂CO₂CH₃ |

Next, some of the pyridone compound [a] are listed with their compound numbers below.

Compounds given by the following formula:

TABLE 2

[Structure: pyridone compound with R³, R⁴ on phenyl, N-CH3, F3C, and pyridone-NH ring]

| Compound number | R³ | R⁴ |
| --- | --- | --- |
| 76 | Cl | F |
| 77 | Cl | H |
| 78 | Br | F |
| 79 | CN | F |
| 80 | CN | H |
| 81 | NO₂ | F |
| 82 | NO₂ | H |
| 83 | Cl | Cl |
| 84 | CN | Cl |

The following are formulation examples when the pyridone compound [d] and the pyridone compound [a] are utilized as herbicidal active ingredients, in which part(s) represents part(s) by weight.

REFERENCE FORMULATION EXAMPLE 1

Fifty parts of each of the compounds 1–84, 3 parts of calcium liginsulfonate, 2 parts of sodium laurylsulfate and 45 parts of synthetic hydrated silicon oxide are well pulverized and mixed to give a wettable powder for each compound.

REFERENCE FORMULATION EXAMPLE 2

Ten parts of each of the compounds 1–84, 14 parts of polyoxyethylene styryl phenyl ether, 6 parts of calcium dodecylbenzenesulfonate, 35 parts of xylene and 35 parts of cyclohexanone are well mixed to give an emulsifiable concentrate for each compound.

REFERENCE FORMULATION EXAMPLE 3

Two parts of each of the compounds 1–84, 2 parts of synthetic hydrated silicon oxide, 2 parts of calcium ligninsulfonate, 30 parts of bentonite and 64 parts of kaolin clay are well pulverized and mixed, and the mixture is well kneaded with water, followed by granulation and drying to give a granule for each compound.

REFERENCE FORMULATION EXAMPLE 4

Twenty-five parts of each of the compounds 1–84, 50 parts of 10% aqueous polyvinyl alcohol solution and 25 parts of water are mixed and pulverized until the mean particle size reaches 5 μm or less to give a suspensible concentrate for each compound.

REFERENCE FORMULATION EXAMPLE 5

Five parts of each of the compounds 1–84 is added to 40 parts of 10% aqueous polyvinyl alcohol solution, and the mixture is emulsified by dispersion with a homogenizer until the mean particle size reaches 10 μm or less, followed by addition of 55 parts of water, to give a concentrated emulsion for each compound.

Next, it is shown that the pyridone compound [d] and the pyridone compound [a] are useful as herbicidal active ingredients.

REFERENCE TEST EXAMPLE 1

Cylindrical plastic pots, each of which has a diameter of 10 cm and a depth of 10 cm, were filled with soil, and then seeded with ivyleaf morning glory and velvetleaf. The test plants were grown in a greenhouse for 10 days. Then, each of the compounds 1, 2, 3, 6, 8, 12, 15, 16, 19, 21, 40, 59 and 76 was formulated into an emulsifiable concentrate according to Reference formulation example 2, and diluted with water containing a spreading agent. The dilution was uniformly sprayed over the foliage of the test plants with a sprayer at a rate of 1000 liters per hectare. After spraying, the test plants were grown in the greenhouse for 12 days, and the herbicidal activity was examined. As a result, each of the compounds of 1, 2, 3, 6, 8, 12, 15, 16, 19, 21, 40, 59 and 76 perfectly controlled the growth of the ivyleaf morning glory and velvetleaf at a dosage of 125 g/ha.

REFERENCE TEST EXAMPLE 2

Cylindrical plastic pots, each of which has a diameter of 10 cm and a depth of 10 cm, were filled with soil, and then seeded with ivyleaf morning glory and velvetleaf. Each of the compounds 1, 2, 3, 6, 8, 12, 15, 16, 19, 21, 40, 59 and 76 was formulated into an emulsifiable concentrate according to Reference formulation example 2, and diluted with water. The dilution was uniformly sprayed over the soil surface with a sprayer at a rate of 1000 liters per hectare. After spraying, the test plants were grown in the greenhouse for 19 days, and the herbicidal activity was examined. As a result, each of the compounds of 1, 2, 3, 6, 8, 12, 15, 16, 19, 21, 40, 59 and 76 perfectly controlled the growth of the ivyleaf morning glory and velvetleaf at a dosage of 500 g/ha.

INDUSTRIAL AVAILABILITY

According to the process of the present invention, the novel pyridine compound [d] having excellent herbicidal activity can be produced beneficially.

The invention claimed is:

1. A pyridone compound of the general formula (a):

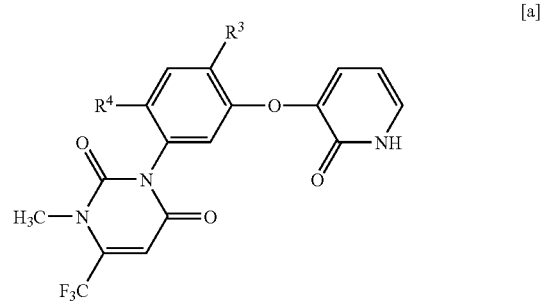

[a]

wherein $R^3$ represents a halogen atom, cyano group or nitro group, and $R^4$ represents a hydrogen atom or halogen atom.

2. The pyridone compound according to claim 1, wherein $R^3$ represents a halogen atom and $R^4$ represents a halogen atom.

3. The pyridone compound according to claim 1, wherein $R^3$ represents a chlorine atom and $R^4$ represents a fluorine atom.

* * * * *